United States Patent
Li et al.

(10) Patent No.: US 9,770,409 B2
(45) Date of Patent: Sep. 26, 2017

(54) AEROSOL FORMULATIONS OF ONDANSETRON AND USES THEREOF

(71) Applicant: LUXENA PHARMACEUTICALS, INC., Sunnyvale, CA (US)

(72) Inventors: Xiaodong Li, Sunnyvale, CA (US); George Lu, Palo Alto, CA (US); Biao Lu, Palo Alto, CA (US)

(73) Assignee: LUXENA PHARMACEUTICALS, INC., Sunnyvale, CA (US)

( * ) Notice: Subject to any disclaimer, the term of this patent is extended or adjusted under 35 U.S.C. 154(b) by 0 days.

(21) Appl. No.: 15/154,431

(22) Filed: May 13, 2016

(65) Prior Publication Data

US 2016/0324775 A1 Nov. 10, 2016

Related U.S. Application Data

(63) Continuation of application No. 14/323,115, filed on Jul. 3, 2014, now abandoned.

(60) Provisional application No. 61/842,791, filed on Jul. 3, 2013, provisional application No. 61/909,972, filed on Nov. 27, 2013.

(51) Int. Cl.
| | |
|---|---|
| *A61K 9/14* | (2006.01) |
| *A61K 9/00* | (2006.01) |
| *A61K 31/4178* | (2006.01) |
| *A61K 9/16* | (2006.01) |
| *A61K 47/26* | (2006.01) |

(52) U.S. Cl.
CPC ............ *A61K 9/0075* (2013.01); *A61K 9/008* (2013.01); *A61K 9/16* (2013.01); *A61K 9/1623* (2013.01); *A61K 31/4178* (2013.01); *A61K 47/26* (2013.01)

(58) Field of Classification Search
USPC ....................................................... 424/489
See application file for complete search history.

(56) References Cited

U.S. PATENT DOCUMENTS

| 5,470,868 A * | 11/1995 | Young ................ A61K 31/4178 |
|---|---|---|
| | | 514/397 |
| 7,022,312 B2 | 4/2006 | Rabinowitz et al. |
| 2003/0035776 A1 | 2/2003 | Hodges et al. |
| 2004/0097509 A1 | 5/2004 | Andrews et al. |
| 2006/0198790 A1 | 9/2006 | Dugger, III et al. |
| 2007/0178166 A1 | 8/2007 | Bernstein et al. |
| 2008/0226736 A1 | 9/2008 | Caponetti et al. |
| 2010/0298397 A1 | 11/2010 | Singh |
| 2011/0160264 A1 | 6/2011 | Myers et al. |
| 2015/0010632 A1 | 1/2015 | Lu et al. |

FOREIGN PATENT DOCUMENTS

| CN | 1498613 A | 5/2004 |
|---|---|---|

OTHER PUBLICATIONS

International search report and written opinion dated Oct. 6, 2015 for PCT/US2015/039139.
Aapro., "Granisetron: an update on its clinical use in the management of nausea and vomiting.", 2004, 9(6), 673-86.
Chow; et al., "Particle engineering for pulmonary drug delivery.", Mar. 2007, 24(3), 411-37.
Cooke; et al., "Oral ondansetron for preventing nausea and vomiting.", Mar. 15, 1994, 51(6), 762-71.
Hornby., "Central neurocircuitry associated with emesis.", Dec. 3, 2001, 111 Suppl 8A, 106S-112S.
Office action dated Mar. 6, 2015 for U.S. Appl. No. 14/323,089.
Ye; et al., "Ondansetron: a selective 5-HT(3) receptor antagonist and its applications in CNS-related disorders.", 2001 Summer, 7(2), 199-213.
U.S. Appl. No. 14/323,089, filed Jul. 3, 2014, Lu, et al.

\* cited by examiner

*Primary Examiner* — Devang Thakor (57) ABSTRACT

Aerosol formulations of ondansetron useful for pulmonary delivery are provided. The formulations are useful in the reduction, elimination or prevention of nausea and vomiting associated with chemotherapy, radiation therapy, and surgery. Also provided are novel methods to treat chemotherapy-induced nausea and vomiting (CINV), radiation-induced nausea and vomiting (RINV), and post-operative nausea and vomiting (PONV) using the inhalation formulations.

18 Claims, 4 Drawing Sheets

AEROSOL FORMULATIONS OF ONDANSETRON AND USES THEREOF

CROSS-REFERENCE TO RELATED APPLICATIONS

The present application is a Continuation of co-pending U.S. Non-Provisional application Ser. No. 14/323,115 filed Jul. 3, 2014, which in turn, claims the benefit under 35 U.S.C. §119 of U.S. Provisional Application Ser. No. 61/842,791, filed on Jul. 3, 2013, and U.S. Provisional Application Ser. No. 61/909,972, filed on Nov. 27, 2013, the contents of which applications are hereby incorporated herein by reference in their entireties.

STATEMENT REGARDING FEDERALLY SPONSORED RESEARCH OR DEVELOPMENT

Not Applicable.

THE NAMES OF THE PARTIES TO A JOINT RESEARCH AGREEMENT

Not Applicable.

INCORPORATION-BY-REFERENCE OF THE MATERIAL ON THE COMPACT DISC

Not Applicable.

BACKGROUND OF THE INVENTION

Field of the Invention

Provided herein are novel aerosol inhalation formulations of ondansetron for pulmonary delivery; and uses thereof in the reduction, elimination or prevention of nausea and vomiting associated with chemotherapy, radiation therapy and surgery. Also provided are methods to treat chemotherapy-induced nausea and vomiting (CINV), radiation-induced nausea and vomiting (RINV), and post-operative nausea and vomiting (PONV) using the inhalation formulations.

Description of the Related Art Including Information Disclosed Under 37 CFR 1.97 and 1.98

Cancer is one of the major causes of death in the modern world. Major therapies to treat cancers include chemotherapy, radiation therapy and surgery. Nausea and vomiting are among the most common side-effects of these treatments. Patients receiving highly emetogenic agents may postpone, or even refuse, potentially curative treatments. Increasing of blood level of serotonin and activation of the 5-HT$_3$ receptors in the chemoreceptor trigger zone in the brain are believed to be related to the emetic responses to cancer treatments [Hornby, 2001].

Figure 1:
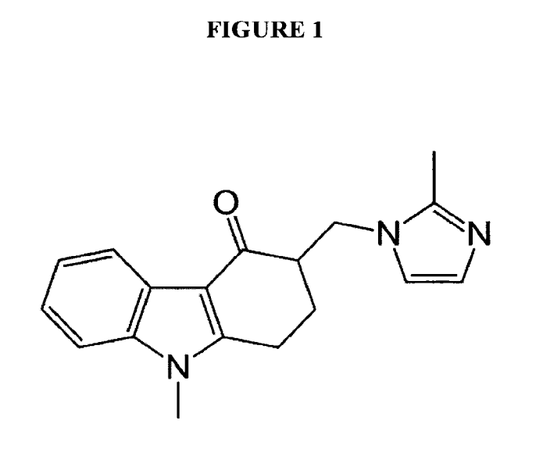
FIG. 1: Skeletal Formula of Ondansetron

Ondansetron is a 5-HT$_3$ receptor antagonist used mainly as an antiemetic often following chemotherapy, radiation therapy and surgery. Ondansetron is believed to block 5-HT$_3$ receptors in the chemoreceptor trigger zone [Cooke et al., 1994]. It is believed to reduce the activity of the vagus nerve, hence the compound deactivates the vomiting center in the medulla oblongata [Ye et al., 2001]. FIG. 1 shows the skeletal formula of ondansetron.

Currently, ondansetron is administered either through injection (slow IV or IM) or as oral tablets. Injection of ondansetron, although effective in reducing or preventing nausea and vomiting, is inconvenient, invasive and causes pain to the patients. Existing forms of oral ondansetron tablets can be difficult to swallow and may be undesirable to some patients requiring anti-emetic therapy, especially those patients who have severe nausea or vomiting.

Thus, there remains a need for new formulations and for novel methods to administer ondansetron. The formulations, and methods described herein are directed toward this end.

BRIEF SUMMARY OF THE INVENTION

In one aspect, the present invention provides novel aerosol formulations comprising ondansetron useful for pulmonary delivery to a subject. In one embodiment, the aerosol formulations are administered by inhalation. In another embodiment, the aerosol formulations are delivered into the circulation via the pulmonary tract. In one embodiment, the subject is a patient such as a cancer patient.

In certain aspects, the present invention provides pharmaceutical aerosol inhalation formulations comprising ondansetron.

In certain aspects, the aerosol formulations of the present invention are useful for the reduction, elimination or prevention of various medical conditions including chemotherapy-induced nausea and vomiting (CINV), radiation-induced nausea and vomiting (RINV), and post-operative nausea and vomiting (PONV).

In another aspect, the present invention provides methods of treating a condition of nausea or vomiting, wherein the method comprises pulmonary administration of a pharmaceutically acceptable amount of the aerosol formulations of the present invention, and wherein the aerosol formulations are administered into the pulmonary tract by inhalation.

In yet another aspect, the present invention provides methods for pulmonary delivery of ondansetron to a subject that comprise having the subject inhale a pharmaceutically acceptable amount of the aerosol formulation of the present invention through the subject's mouth into the circulation via the pulmonary tract. In one embodiment, the subject is a cancer patient.

In yet another aspect, the present invention provides a method for pulmonary delivery of ondansetron to a subject, where the method comprises having the subject inhale a pharmaceutically acceptable amount of the aerosol formulation of the present invention through the subject's nose into the circulation via the pulmonary tract. In one embodiment, the subject is a cancer patient.

In yet another aspect, with respect to the aerosol formulations or methods of the present invention, the pulmonary administration of the aerosol formulations minimizes the first pass metabolism before the drug reaches the target receptors since there is rapid transport from the alveolar epithelium into the circulation. In addition, the pulmonary administration of the aerosol formulations of the present invention by inhalation avoids gastrointestinal intolerance which is typical for nausea and vomiting sufferers.

Other objects and advantages will become apparent to those skilled in the art from a consideration of the ensuing detailed description.

DETAILED DESCRIPTION OF THE INVENTION

The present invention provides novel aerosol formulations comprising ondansetron useful for pulmonary delivery to a subject. In one embodiment, the aerosol formulations are administered by inhalation. In another embodiment, the aerosol formulations are delivered into the circulation via the pulmonary tract. The subject for whom the aerosol formulations are administered may be a mammal, such as a human. In one embodiment, the subject is a patient; in particular, the subject is a cancer patient.

The present invention also provides pharmaceutical aerosol inhalation formulations comprising powdered ondansetron. In one embodiment, with respect to the aerosol inhalation formulation, the mass median aerodynamic diameter (MMAD) of powdered ondansetron is between 0.05 and 20 microns, preferably the powdered ondansetron has an MMAD between 0.5 and 5 microns. In another embodiment, the aerosol formulations are useful for pulmonary delivery of ondansetron to a subject. In one embodiment, the subject is a cancer patient.

The present invention provides inhalable pharmaceutical aerosol formulations comprising powdered ondansetron, wherein the MMAD of powdered ondansetron is between 0.05 and 20 microns; and wherein the formulations are useful for pulmonary delivery to a subject, where the subject is a cancer patient. In one embodiment, the aerosol formulations are delivered into the circulation via pulmonary tract of the subject and the subject is a cancer patient.

In certain aspects, the aerosol formulations of the present invention are useful for the reduction, elimination, or prevention of nausea and vomiting associated with various medical conditions including chemotherapy-induced nausea and vomiting (CINV), radiation-induced nausea and vomiting (RINV), and post-operative nausea and vomiting (PONV).

In certain aspects, the aerosol formulations of the present invention are administered by subjects via an inhaler allowing ondansetron to enter the circulation rapidly.

In certain aspects, the aerosol formulations of the present invention provide a novel route of administration of ondansetron to subjects who have severe nausea or vomiting, or to subjects who are not willing to or not able to swallow or to be injected.

In certain aspect, the aerosol formulations of the present invention contains ondansetron that is in a solute form. In certain aspect, the aerosol formulations of the present invention contains ondansetron that is in a powdered form.

In certain aspect, the aerosol formulations of the present invention contains ondansetron that is in a powdered form, and the powdered ondansetron is in a dry powder form.

In certain aspect, the aerosol formulations of the present invention contains ondansetron that is in a powdered form, and the powdered ondansetron is in a suspension. In certain aspect, the powdered ondansetron suspension is in a liquid selected from a group consisting of propellants, hybrid propellants, propellants with stabilizers, propellants with surfactants, propellants with diluents, propellants with cosolvents, water, buffer, and combinations thereof.

In certain aspect, the aerosol formulations of the present invention contains ondansetron that is a solute in a solution, and the solvent is selected from a group consisting of propellants, hybrid propellants, cosolvents, cosolvent mixture, organic solvents, water, buffers, and combinations thereof.

When the ondansetron in the aerosol formulations is in a powdered form, the powdered ondansetron is produced by one or more particle engineering processes [Chow et al., 2007]. For example, the powdered ondansetron may be produced by a mechanical micronization operation selected from the group consisting of crushing, cutting, bashing, milling, and grinding. In another embodiment, the powdered ondansetron is produced by a precipitation process, such as spray drying, solution precipitation, lyophilization, or combinations of the foregoing. Yet in another embodiment, the powered ondansetron is produced by one of more precipitation processes followed by one or more mechanical micronization processes.

In one embodiment, the powdered ondansetron of the aerosol formulations is produced by a spray drying process. The spray drying process may be followed by a cyclone separation/filtering process.

In another embodiment, the powdered ondansetron of the aerosol formulations is produced by a direct controlled crystallization process. The direct controlled crystallization process may utilize an antisolvent precipitation technique. Moreover, the size range of the crystallines may be controlled by one or more growth-retarding stabilizing additives.

In yet another embodiment, the powdered ondansetron of the aerosol formulations is produced by a supercritical fluid process. The supercritical fluid process is selected from the group consisting of rapid expansion of supercritical solution (RESS), solution enhanced diffusion (SEDS), gas-anti solvent (GAS), supercritical antisolvent (SAS), precipitation from gas-saturated solution (PGAS), precipitation with compressed antisolvent (PCA) and aerosol solvent extraction system (ASES).

In a particular embodiment, with respect to the aerosol formulations, the powdered ondansetron is produced by supercritical fluid process, and the process is rapid expansion of supercritical solution (RESS) process. In another particular embodiment, the process is solution enhanced diffusion (SEDS) process. In yet another particular embodiment, the process is gas-anti-solvent (GAS) process. In yet another particular embodiment, the process is supercritical-anti-solvent (SAS) process. In yet another particular embodiment, the process is precipitation from gas-anti-solvent (PGAS) process. In yet another particular embodiment, the process is precipitation with compressed anti-solvent (PCA) process. In yet another particular embodiment, the process is aerosol solvent extraction system (ASES) process. In yet another particular embodiment, the process is any combinations of the foregoing.

In a more particular embodiment, with respect to the aerosol formulations, the powdered ondansetron is produced by a supercritical fluid process, and the supercritical fluid process is rapid expansion of supercritical solution process.

In one embodiment, with respect to the aerosol formulations, the mean geometric diameter of powdered ondansetron is at least 0.01 microns, at least 0.05 microns, at least 0.1 microns, at least 0.25 microns, at least 0.5 microns, at least 0.75 microns, at least 0.9 microns, at least 1 microns, at least 1.25 microns, at least 1.5 microns, at least 1.75 microns, or even at least 2.0 microns. The mean geometric diameter of powdered ondansetron is at most 20 microns, at most 15 microns, at most 12 microns, at most 10 microns, at most 9 microns, at most 8 microns, at most 7.5 microns, at most 7 microns, at most 6.5 microns, at most 6.0 microns, at most 5.75 microns, at most 5.5 microns, at most 5.25 microns, at most 5.0 microns, at most 4.75 microns, at most 4.5 microns, at most 4.25 microns, at most 4.0 microns, at most 3.75 microns, at most 3.5 microns, at most 3.25 microns, and even at most 3.0 microns. The mean geometric diameter of powdered ondansetron generally ranges from between 0.05 and 30 microns, preferably between 0.1 and 20 microns, between 0.2 and 15 microns, between 0.3 and 10 microns, and more preferably between 0.5 and 5 microns. Advantageously, the mean geometric diameter of powdered ondansetron is between 1 and 3 microns.

In a particular embodiment, with respect to the aerosol formulations, the mean geometric diameter of powdered ondansetron is between 0.05 and 20 microns, preferably between 0.5 and 4 microns, more preferably between 1 and 3 microns.

In one embodiment, with respect to the aerosol formulations, the powdered ondansetron has an MMAD of at least 0.01 microns, at least 0.05 microns, at least 0.1 microns, at least 0.25 microns, at least 0.5 microns, at least 0.75 microns, at least 0.9 microns, at least 1 microns, at least 1.25 microns, at least 1.5 microns, at least 1.75 microns, or even at least 2.0 microns. The MMAD of powdered ondansetron is at most 30 microns, at most 20 microns, at most 15 microns, at most 10 microns, at most 9 microns, at most 8 microns, at most 7.5 microns, at most 7 microns, at most 6.5 microns, at most 6.0 microns, at most 5.75 microns, at most 5.5 microns, at most 5.25 microns, at most 5.0 microns, at most 4.75 microns, at most 4.5 microns, at most 4.25 microns, at most 4.0 microns, at most 3.75 microns, at most 3.5 microns, at most 3.25 microns, and even at most 3.0 microns. Generally, the MMAD of the powdered ondansetron is between 0.05 and 30 microns, preferably between 0.1 and 20 microns, between 0.2 and 15 microns, more preferably between 0.3 and 10 microns, between 0.5 and 5 microns, and especially between 1 and 3 microns.

In a particular embodiment, with respect to the aerosol formulations, the powdered ondansetron has an MMAD between 0.05 and 20 microns, preferably between 0.5 and 4 microns, and more preferably between 1 and 3 microns.

In one embodiment, with respect to the aerosol formulations, the mean geometric diameter and the MMAD of powdered ondansetron are similar. Alternatively, in another embodiment, the mean geometric diameter and the MMAD of powdered ondansetron are different. In one embodiment, where the mean geometric diameter and the MMAD of powdered ondansetron are different, the difference is due to the morphology of the ondansetron particles.

The powdered ondansetron may be a solvate, hydrate, organic salt, inorganic salt, ester, or free base. The powdered ondansetron may also be amorphous, crystalline, or polymorphous. Preferably, the ondansetron is a chloride, bromide, iodide, mesylate, methanesulphonate, para-toluenesulphonate, or methyl sulphate salt. More preferably, the ondansetron is in the form of a hydrochloride, anhydrous, monohydrate or dihydrate.

In one embodiment, the ondansetron particles of the aerosol formulations are amorphous.

In one embodiment, the ondansetron particles of the aerosol formulations are crystallines. In another embodiment, the shape of the ondansetron particles is one of the group consisting of spherical, ellipsoidal, cubical, diamond, rectangular, orthorhombic, triangular, hexagonal, needlelike, and porous. Preferably, the ondansetron particles of the aerosol formulations are spherical.

In one embodiment, the ondansetron particles of the aerosol formulations are polymorphous. In another embodiment, the shapes of the ondansetron particles are two of more from the group consisting of spherical, ellipsoidal, cubical, diamond, rectangular, orthorhombic, triangular, hexagonal, needlelike, and porous.

In one embodiment, with respect to the aerosol formulations, the proportion of ondansetron particles with aerodynamic diameters less than 5 µm is at least 5%, at least 10%, at least 15%, at least 20%, at least 25%, at least 30%, at least 35%, at least 40%, at least 45%, at least 50%, at least 55%, at least 60%, at least 70%, and preferably at least 70%. In another embodiment, the proportion of ondansetron particles with aerodynamic diameters less than 5 µm is at most 100%, at most 99%, at most 95%, at most 90%, at most 85%, at most 80%, at most 75%, at most 70%, at most 65%, at most 60%, at most 55%, at most 50%, at most 45%, at most 40%, at most 35%, at most 30%, at most 25%, at most 20%, at most 17.5%, at most 15%, and even at most 12.5%.

In one embodiment, with respect to the aerosol formulations, the proportion of ondansetron particles with aerodynamic diameters less than 5 µm is 10% to 100%, preferably from 70% to 100%. In another embodiment, the proportion of ondansetron particles with aerodynamic diameters less than 5 µm is from 20 to 80%, preferably from 30% to 70%. In a further embodiment, the proportion of ondansetron particles with aerodynamic diameters less than 5 µm is 10% to 30%.

In one embodiment, with respect to the aerosol formulations, the fine particle fraction (FPF) of ondansetron is 10% to 100%. In certain embodiments, the minimum FPF is 50%, for instance, at least 55%, at least 60%, at least 65%, at least 70%, at least 75%, at least 80%, at least 85%, and even at least 90%. In one embodiment, the FPF of ondansetron is from 70% to 100%. The FPF of ondansetron may also range from 30% to 70%. In another embodiment, the maximum FPF of ondansetron is 50% or less, for instance, the maximum FPF of ondansetron is at most 40%, at most 35%, at most 30%, at most 25%, at most 20%, at most 17.5%, at most 15%, at most 12.5%, and even at most 10%. In one embodiment, the FPF of the ondansetron is 10% to 30%.

In the aerosol formulations according to the invention, the ondansetron has respirable fraction of 10% or more, preferably 15% or more, 20% or more, 25% or more, 35% or more, 40% or more, 45% or more, 50% or more, more preferably 75% or more, and even 90% or more.

In one embodiment, the aerosol formulations do not comprise an excipient.

In another embodiment, the aerosol formulations further comprise a pharmaceutically acceptable excipient. The excipient is any excipient acceptable for pulmonary delivery. More particularly, the excipient is any inhalable excipient.

In aerosol formulations containing an excipient, the excipient is selected from the group consisting of carbohydrates, amino acids, polypeptides, lipids, buffers, salts, polyalcohols, and mixtures thereof. In yet another embodiment, the excipient is selected from the group consisting of galactose, mannose, sorbose, lactose, glucose, trehalose, raffinose, maltodextrins, dextrans, mannitol, xylitol, and mixtures thereof. In yet another embodiment, the excipient is selected from the group consisting of alanine, glycine, tryptophan, tyrosine, leucine, phenylalanine, and mixtures thereof. In yet another embodiment, the excipient is selected from the group consisting of oleates, stearates, myristates, alkylethers, alkyl arylethers, sorbates, polyvinylpyrrolidone (PVP) and mixtures thereof. In yet another embodiment, the excipient is selected from the group consisting of 1,1,1,2-tetrafluoroethane (P134a), 1,1,1,2,3,3,3-heptafluoro-n propane (P227), 2H, 3H-perfluoropentane (HPFP) and mixtures thereof. In yet another embodiment, the excipient is any combinations of the foregoing.

In certain embodiments, the aerosol formulations are pressurized metered dose formulations. In certain embodiments, the aerosol formulations are dry powder formulations. In certain embodiments, the aerosol formulations are nebulizer formulations.

Dry Power Formulations

In a particular embodiment, the formulation is a dry powder formulation containing an excipient, where the excipient is lactose, glucose, or a mixture of lactose and glucose.

In the dry powder formulations containing a pharmaceutically acceptable excipient, the excipient consists of powders with an average particles size of <5 to 200 microns, from 1 to 150 microns, or from 5 to 100 microns. The excipient may consists of powders of the same substance with an average particle size of <5 to 200 microns, from 1 to 150 microns, or from 5 to 100 microns. There may also be a mixture of powders in which the average particle size is from <5 to 200 microns, from 1 to 150 microns, or from 5 to 100 microns.

In particular, where the dry powder formulations further comprise a pharmaceutically acceptable excipient and the excipient consists of powders with an average particle size of <5 to 200 microns, the excipient may be a mixture of the same substance with different particle size distributions. For example, in one embodiment the pharmaceutically acceptable excipient having an average particle size of <5 to 200 microns with different particle size distributions is a mixture of coarser powders and finer powders of the same substance, where the finer powders have an average particle size from <5 to 50 microns and the coarser powders have an average particle size of 50 to 200 microns. The finer powders may have an average particle size from <5 to 45 microns, from 10 to 40 microns, from 15 to 35 microns, or from 20 to 30 microns, while the coarser powders may have an average particle size from 60 to 90 microns, from 65 to 85 microns, or from 70 to 80 microns. Alternatively, the finer powders may have an average particle size from 1 to 10 microns, from 1 to 7.5 microns, from 1 to 5 microns, or from 2 to 5 microns, while the coarser powders may have an average particle size from 20 to 60 microns, from 20 to 25 microns, from 30 to 60 microns, from 40 to 60 microns, or from 50 to 60 microns. In some embodiments, the coarser powders have an average particle size from 50 to 90 microns, from 65 to 85 microns, or from 70 to 80 microns. The proportion of finer excipient powders may be 0.1% to 99% of the total amount of excipient powders.

In another embodiment, with respect to the dry powder formulations, the pharmaceutically acceptable excipient having an average particle size of <5 to 200 microns with different particle size distributions is a mixture of finer powders, coarser powders, and much coarser powders of the same substance, where the finer powders have an average particle size of <5 to 20 microns, the coarser powders have an average particles size of 20 to 60 microns, and the much coarser powders have an average particles size of 60 to 200 microns. Preferably, the finer powders have an average particle size of <5 to 10 microns, the coarser powders have an average particles size of 25 to 45 microns, and the much coarser powders have an average particles size of 75 to 90 microns. The proportion of finer excipient powders may be 0.1% to 99% of the total amount of excipient powders.

In addition, in the dry powder formulations, the pharmaceutically acceptable excipient may be a mixture of different substances with similar particle size distributions in which the average particle size is from <5 to 200 microns or from 5 to 100 microns.

Advantageously, the pharmaceutically acceptable excipient in the dry powder formulations is a mixture of different substances with different particle size distributions in which the average particle sizes are from <5 to 200 microns. Namely, the pharmaceutically acceptable excipient of the dry powder formulations is a mixture of finer powders having an average particle size of <5 to 50 microns and coarser powders with an average particles size of 50 to 200 microns; the finer powders and the coarser powders being different substances. The proportion of finer excipient powders may be 0.1% to 99% of the total amount of excipient powders.

In another embodiment, the pharmaceutically acceptable excipient of the dry powder formulations is a mixture of finer powders having an average particle size of <5 to 20 microns, coarser powders having an average particles size of 20 to 60 microns, and much coarser powders having an average particles size of 60 to 200 microns; the finer powders, the coarser powders, and the much coarser powders being different substances. Preferably, the finer powders have an average particle size of <5 to 15 microns, the coarser powders have an average particles size of 30 to 50 microns, and the much coarser powders have an average particles size of 70 to 90 microns. The proportion of finer excipient powders may be 0.1% to 99% of the total amount of excipient powders.

In embodiments where the pharmaceutically acceptable excipient of the dry powder formulations is a mixture of finer powders and coarser powders; the powdered ondansetron may be blended with the finer excipient powders first, and then the mixture of the powdered ondansetron and the finer powders are blended with the coarser excipient powders. Alternatively, the powdered ondansetron may be blended with the finer excipient powders and the coarser excipient powders separately, and then each of the blended excipient mixtures (i.e., finer excipient powders with powdered ondansetron and coarser excipient powders with powdered ondansetron) are blended with each other.

In embodiments were the pharmaceutically acceptable excipient of the dry powder formulations is a mixture of finer powders, coarser powders, and much coarser; the powdered ondansetron may be sequentially blended with the finer excipient powders, the coarser excipient powders, and the much coarser excipient powders. Alternatively, the powdered ondansetron is blended with the finer excipient powders, the coarser excipient powders, and the much coarser excipient powders separately, and then the mixtures (i.e., finer excipient powders with powdered ondansetron, coarser excipient powders with powdered ondansetron, and much coarser excipient powders with ondansetron) are blended with each other.

The content of the powdered ondansetron in the dry powder formulations ranges from 0.05% to about 100% of the total composition of formulation, preferably from about 0.05% to about 50%, from about 0.05% to about 45%, from about 0.05% to about 40%, from about 0.05% to about 35%, from about 0.05% to about 30%, from about 0.05% to about 25%, from about 0.05% to about 20%, from about 0.05% to about 15%, or from about 0.05% to about 10% of the total composition of formulation.

The content of the powdered ondansetron in the dry powder formulations may also range from about 0.1% to about 100%, from about 0.1% to about 50%, from about 0.1% to about 45%, from about 0.1% to about 40%, from about 0.1% to about 35%, from about 0.1% to about 30%, from about 0.1% to about 25% of the total composition of formulation, from about 0.1% to about 20%, from about 0.1% to about 15%, or from about 0.1% to about 10% of the total composition of formulation, preferably from about 1% to about 10% of the total composition of formulation, and more preferably from about 5% to about 10% of the total composition of formulation. In a particular embodiment, with respect to the formulations, the powdered ondansetron is about 10% of the total composition of formulation.

Generally, the dry powder formulations contain 0.1-40 mg of the powdered ondansetron, preferably from 0.5-20 mg, from 5-16.

In a particular embodiment, the dry powder formulations comprise ondansetron and lactose. The dry powder formulations containing lactose comprise ondansetron, finer lactose, and coarser lactose, or ondansetron, finer lactose, and much coarser lactose ondansetron, or finer lactose, coarser lactose, and much coarser lactose. For example, the dry powder formulations may comprise about 0.5 to about 20 mg of ondansetron, about 0.001 to about 2 g of finer lactose, and about 0.001 to about 2 g of coarser lactose. For example, in dry powder formulations containing ondansetron and lactose or glucose, the amount of the ondansetron is from 0.5-20 mg, and the amount of lactose or glucose is about 0.001 g to about 2.5 g. Preferably, the amount of ondansetron is about 0.5 to about 20 mg and the amount of lactose or glucose is about 1 to about 200 mg.

In yet another particular embodiment, the dry powder formulations comprise ondansetron and glucose. The dry powder formulations containing glucose comprise ondansetron, finer glucose, and coarser glucose, or ondansetron, finer glucose, coarser glucose, and much coarser glucose. In yet another particular embodiment, the dry powder formulations comprise about 0.5 to about 20 mg of ondansetron, about 0.001 to about 2 g of finer glucose, and about 0.001 to about 2 g of coarser glucose. For example, the dry powder formulations may comprise about 0.5 to about 20 mg of ondansetron, about 1 to about 200 mg of finer glucose, and about 1 to about 200 mg of coarser glucose.

In yet another particular embodiment, the dry powder formulations comprise ondansetron, lactose, and glucose. The dry powder formulations comprising ondansetron, lactose, and glucose may comprise ondansetron, finer lactose, and coarser glucose or ondansetron, finer glucose, and coarser lactose. For example, the dry powder formulations may comprise about 0.5 to about 20 mg of ondansetron, from about 0.001 to about 2 g of lactose, and from about 0.001 to about 2 g of glucose. In one particular embodiment, the dry powder formulations comprise from about 0.5 to about 20 mg ondansetron, from about 0.001 to 2 g of finer lactose, and from about 0.001 to about 2 g of coarser glucose. In an alternative embodiment, the formulation comprises from about 0.5 to about 20 mg of ondansetron, from about 0.001 to about 2 g of finer glucose, and from about 0.001 to about 2 g of coarser lactose.

The aerosol formulations of the present invention are uniform and homogeneous. The uniformity/homogeneity of the aerosol formulations is measured by drawing 3 or more samples from the formulation, dissolving in mobile, and testing for concentration of the active pharmaceutical ingredient (API, ondansetron) in the formulation by HPLC. The uniformity of the aerosol formulations is expressed by the relative standard deviation (% RSD) of the API concentration. The aerosol formulations have an RSD % less than 5%, less than 4%, less than 3%, less than 2.5%, less than 2.25%, less than 2.0%, less than 1.75%, less than 1.5%, less than 1.25%, less than 1.0%, less than 0.75%, less than 0.5%, less than 0.25%, and even less than 0.25%.

The discharge capacity or percent recovery of the aerosol formulations is measurable with a Next Generation Pharmaceutical Impactor (NGI). In this device, powders are drawn by vacuum into different chambers representing the lung, each chamber corresponding to a different range of aerodynamic particle size. NGI data includes mass median aerodynamic diameter (MMAD), and fine particle fraction (FPF). The FPF is generally assumed to represent the fraction of particles that would deposit in vivo in the "deep lungs," or particles that have an aerodynamic diameter of equal to or less than 5 µm. The discharge capacity or percent recovery of the aerosol formulations of the present invention is at least 70%, at least 75%, at least 80%, at least 85%, at least 90%, at least 91%, at least 92%, at least 93%, at least 94%, at least 95%, at least 96%, at least 97%, at least 98%, and even at least 99%, as measured by NGI.

The present inventors have observed that the inclusion of fine excipient particles increases the FPF while decreasing the MMAD. The inclusion of coarse excipient powders alone resulted in a FPF percent delivery of 7 to 8% where the coarse particles were lactose particles having a D10 of 3~6 µm, a D50 of 20~25 µm, and a D90 of 50~60 am (LAC-TOHALE® 201 (LH201)), or lactose particles having a D10 of ~4 am, a D50 of ~55 µm, and D90 a of ~170 µm (RESPITOSE® ML001 (ML001)). However, a combination of the coarse lactose particles ML001 (D10 of ~4 µm, a D50 of ~55 µm, and D90 a of ~170 µm) with fine lactose excipient particles having a D50<5 µm and a D90≤10 µm increased the FPF percent delivery. The FPF percent delivery increased further where the coarse particles that were mixed with the fine particle had a D10 of ~30 µm, a D50 of ~60 am, and a D90 was ~100 µm (RESPITOSE® SV003 (SV003)).

In the present invention, each of the aerosol formulations containing coarse and fine lactose particles achieved a 3-5% increase in the delivery of FPF when the humidity of the environment during the aerodynamic performance testing was controlled to have a relative humidity (RH) of 50% rather than the ambient 20% RH. It is believed that the higher-than-ambient humidity, which is more representative of the environment in the human inhalation route, further increases the disaggregation by reducing the surface-energy-induced-aggregation when the formulation is inhaled into the impator.

Typically, the dry powdered formulations are administered by a dry powder inhaler, a dry powder dispenser, or a dry powder delivery device. The inhaler may be a single dose or multi-dose inhaler. Suitable inhalers may include SPINHALER®, ROTAHALER®, AEROLIZER®, INHALATOR®, HANDIHALER®, DISKHALER®, DISKUS®, ACCUHALER®, AEROHALER®, ECLIPSE®, TURBOHALER®, TURBUHALER®, EASYHALER®, NOVOLIZER®, CLICKHALER®, PULVINAL®, NOVOLIZER®, SKYEHALER®, XCELOVAIR®, PULVINA®, TAIFUN®, MAGHALER®, TWISTHALER®, JETHALER®, FLOWCAPS®, XCAPS®, TWINCAPS®, CYCLOHALER®, TURBOSPIN®, AIR DPI®, ORBITAL®, DIRECTHALER®, or an inhaler that is newly developed.

Pressurized Metered Dose Formulations (pMDI Formulations)

In another particular embodiment, the formulation is a pMDI formulation containing an excipient, where the excipient selected from the group consisting of oleates, stearates, myristates, alkylethers, alkyl arylethers, sorbates, and mixtures thereof. In the pMDI formulations, the excipient may include sorbitan trioleate, isopropyl myristate, or lecithin. Additional excipients for the pMDI formulations include oleic acid or oleic acid esters and polyvinylpyrrolidone (PVP).

In certain embodiments, the pMDI formulations do not include a propellant. However, the pMDI formulations generally include a propellant, especially a hydrofluoroalkane propellant. The hydrofluoroalkane propellants for the pMDI formulations are selected from the group consisting of 1,1,1,2-tetrafluoroethane (P134a), 1,1,1,2,3,3,3-heptafluoron propane (P227), and mixtures P134a and P227. Another suitable propellant for the pMDI formulations is 2H, 3H-perfluoropentane (HPFP).

The pMDI formulations may further include a diluent or a mixture of diluents. The pMDI formulations may also include a surfactant or a mixture of surfactants. Exemplary surfactants are selected from the group consisting of alkylethers, alkyl arylethers, laurates, myristates, oleates, sorbates, stearates, propylene glycol, lipids, and combinations thereof. Preferred surfactants are oleates, sorbates, stearates, propylene glycol, and combinations thereof.

In certain embodiments, the pMDI formulations do not comprise a co-solvent. However, in alternate embodiments, the pMDI formulations contain a co-solvent or a mixture of co-solvents. The pMDI formulations may include a co-solvent selected from $C_{2-6}$ alcohols, polyols, cineole, citral, lactic acid oligomers, or poly(ethylene glycols).

The pMDI formulations may comprises ethanol as a co-solvent. The content of ethanol in the pMDI formulations is no more than 25% (w/w), no more than 20% (w/w), no more than 15% (w/w), no more than 10% (w/w), no more than 8% (w/w), preferably no more than 5% (w/w) of ethanol, no more than 2.5% (w/w), and more preferably no more than 1% (w/w) of ethanol.

The content of the ondansetron in the pMDI formulations is from about 0.01% to about 20%, from about 0.01% to about 10%, from 0.01% to about 5%, from about 0.01% to about 2%, from about 0.01% to about 1%, or from about 0.01% to about 0.5% of the total composition of the formulation. In a particular embodiment, with respect to the pMDI formulations, the content of the ondansetron is from about 0.1% to about 0.5% of the total composition of the formulation.

In a particular embodiment, the pMDI formulations comprise ondansetron and at least one selected from P134a and P227. In such pMDI formulations, based on the size of the canister, the amount of ondansetron is from 0.1-400 mg, and the amount of P134a and/or P227 is about 0.5 g to about 50 g. In certain embodiments, the pMDI formulation contains ondansetron and P134a, where the amount of ondansetron is from about 0.1 to about 400 mg, preferably about 1-200 mg, and the amount of P134a is from 0.5 g to about 50 g, preferably about 10 g to 20 g. Similarly, the pMDI formulation may contains ondansetron and P227, where the amount of ondansetron is from about 0.1 to about 400 mg, preferably about 1-200 mg, and the amount of P227 is from 0.5 g to about 50 g, preferably about 10 g to 20 g. In pMDI formulations containing ondansetron, P134a, and P227, the amount of ondansetron is from about 0.1 to about 400 mg, preferably about 1-200 mg, the amount of P134a about 0.5 g to about 50 g, and the amount of P227 is about 0.5 g to about 50 g.

In further embodiments, the pMDI formulation comprises ondansetron, P134a and/or P227, and isopropyl myristate. In certain embodiments, the pMDI formulations contain ondansetron, P134a and/or P227, and propylene glycol. In addition, the pMDI formulations may contain ondansetron, P134a and/or P227, and isopropyl laurate.

In certain embodiments, the pMDI formulations of the present invention contains ondansetron that is a solute in a solution, and the solvent is selected from a group consisting of propellants, hybrid propellants, cosolvents, cosolvent mixture, organic solvents, water, buffers, and combinations thereof.

In certain embodiments, the pMDI formulations of the present invention contains ondansetron that is in a powdered form in a suspension, and the suspension is in a liquid selected from a group consisting of propellants, hybrid propellants, propellants with stabilizers, propellants with surfactants, propellants with diluents, propellants with cosolvents, water, buffer, and combinations thereof.

In a particular embodiment, the pMDI formulations of the present invention contains ondansetron that is a solute in a solution, wherein the solubility of ondansetron is more than 0.01% w/w, more than 0.1% w/w, or more than 1%.

In a particular embodiment, the pMDI formulations of the present invention contains ondansetron that is in a powdered form in a suspension, wherein the solubility of ondansetron is less than 0.1% w/w, less than 0.01% w/w, or less than 0.001%.

Typically, the pMDI formulations are administered by an actuator, a metered dose inhaler, an aerosol dispenser, or an aerosol delivery device.

The present invention also provides methods of treating a condition of nausea or vomiting, wherein the method comprises pulmonary administration of a pharmaceutically acceptable amount of the aerosol formulations of the present invention; and wherein the formulations are administered into the pulmonary tract by inhalation. The pulmonary delivery of ondansetron to a subject is carried out by having the subject inhale a pharmaceutically acceptable amount of the aerosol formulation of the present invention through the subject's mouth. Additionally or alternatively, the pulmonary delivery of ondansetron to a subject is accomplished by having the subject inhale a pharmaceutically acceptable amount of the aerosol formulation of the present invention through the subject's nose.

In one embodiment, the pharmaceutically acceptable amount is produced by introducing the ondansetron into a gas stream. Specifically, the pharmaceutically acceptable amount is produced by introducing the ondansetron into a gas stream, and the gas stream is the subject's inspiratory breath.

In one embodiment, with respect to the methods, the pharmaceutically acceptable amount contains about 0.1 mg to about 40 mg of ondansetron and the total dosage is from about 0.1 mg to about 40 mg.

Preferably, the pharmaceutically acceptable amount contains less than about 40 mg, less than about 30 mg, less than about 25 mg, less than about 20 mg, less than about 15 mg, or less than about 10 mg of ondansetron. In another embodiment, the pharmaceutically acceptable amount contains more than about 0.1 mg, more than about 0.5 mg, more than about 1 mg, more than about 2 mg, or more than about 5 mg of ondansetron. More preferably, the pharmaceutically acceptable amount contains about 8 mg of ondansetron.

The total dosage of ondansetron per day is about 0.1 mg to about 40 mg, about 0.5 mg to about 30 mg, about 1 mg to about 25 mg, about 5 mg to about 20 mg, about 8 mg to about 16 mg of ondansetron per day.

With the dry powder formulations, the pharmaceutically acceptable amount of ondansetron is produced by releasing blended powders containing powdered ondansetron from a container such as a capsule or a blister by using a device such as a dry powder inhaler. A device may be loaded with one or more capsules/blisters at a time. The pharmaceutically acceptable amount is produced through one, two or multiple actuations. The releasing amount of one actuation is preferably equal to the formulation stored in one capsule or blister. Whereas with the pMDI formulations, the pharmaceutically acceptable amount of ondansetron is produced by releasing a propellant containing ondansetron from a container such as a canister by using a device such as a pMDI inhaler. The canister may be actuated by pressing an actuator or by inhalation. The pharmaceutically acceptable amount is produced through one, two or multiple actuations. The releasing amount of one actuation is preferably less than the formulation stored in one canister. The releasing amount is metered.

After administration to a subject, ondansetron in blood plasma reaches a maximum concentration (Cmax) of 1-5000 ng/mL in the subject, preferably of 2-2000 ng/mL, and more preferably of 5-1000 ng/mL in a subject.

Delivery of the aerosol formulations through the pulmonary tract of a subject provides a Cmax of ondansetron in blood plasma that is about 0.05 to about 1, about 0.1 to about 0.8, about 0.2 to about 0.6, or about 0.3 to about 0.4 times of the Cmax achieved following intravenous bolus delivery of ondansetron. Moreover, delivery of the aerosol formulations through the pulmonary tract of a subject to provides a Cmax of ondansetron in blood plasma that is about 0.1 to about 1.5, about 0.2 to about 1.25, about 0.4 to about 1.1, or about 0.8 to about 1.05 times of the Cmax achieved following oral delivery of ondansetron.

In addition, the ondansetron in blood plasma reaches maximum concentration at (Tmax) 1 minute to 2 hours after dose in a subject, preferably the Tmax is 2 minutes to 1 hour after dose in a subject, and even 5 minutes to 30 minutes after dose in a subject. Delivery of the aerosol formulations through the pulmonary tract of a subject provides a Tmax of ondansetron in blood plasma that is about 0.01 to about 1.5, about 0.05 to about 1, about 0.1 to about 0.8, about 0.2 to about 0.6, or about 0.3 to about 0.4 times of the Tmax achieved following oral delivery of ondansetron.

The area under curve (AUC) of ondansetron in blood plasma of a subject ranges from 2-50000 ng*h/mL, preferably from 5-20000 ng*h/mL, and more preferably from 10-10000 ng*h/mL. Delivery of the aerosol formulations through the pulmonary tract produces a mean AUC of ondansetron in blood plasma that is about 0.1 to 1.5, about 0.2 to about 1.25, about 0.4 to about 1.1, or about 0.8 to about 1.05 times of the mean AUC achieved following intravenous bolus delivery of ondansetron. In one embodiment, the AUC is about the same as that is achieved following intravenous bolus delivery of ondansetron. Similarly, delivery of the aerosol formulations through the pulmonary tract produces a mean total AUC of ondansetron in blood plasma that is about 0.1 to about 1.5, about 0.2 to about 1.25, about 0.4 to about 1.1, or about 0.8 to about 1.05 times of the AUC achieved following oral delivery of ondansetron. In one embodiment, the AUC is about the same as that is achieved following oral delivery of ondansetron.

In one embodiment, the aerosol and dry powder formulations and the method are useful for the reduction, elimination, or prevention of nausea and vomiting, where the nausea and vomiting are chemotherapy-induced nausea and vomiting, radiation-induced nausea, or vomiting and post-operative nausea and vomiting.

In one embodiment, the subject is a cancer patient; in particular, a cancer patient undergoing chemotherapy, radiotherapy, or a surgery. Additionally, the cancer patient may suffer from nausea and/or vomiting related to the chemotherapy, radiotherapy, or surgery.

The powdered ondansetron of the aerosol formulations may be prepared by dissolving the bulk ondansetron in distilled water with co-solvents, to form a solution; spray drying the solution, to obtain powered ondansetron; separating and filtering the powdered ondansetron according to their sizes with a cyclone; milling and grinding the powdered ondansetron to further reduce the size of powered ondansetron; and collecting and analyzing the precipitated ondansetron powder. During the milling and grinding, the milling and grinding forces and timing are optimized so that the particle size distribution of the processed ondansetron is from about 0.5 to about 5 μm; and the mean volume diameter is of about 2-3 μm.

The powdered ondansetron of the aerosol and dry powder formulations may also be prepared by dissolving the bulk ondansetron in distilled water, to form a solution; spray drying the solution with temperature in a drying vessel; separating and filtering the powdered ondansetron according to their sizes with a cyclone; and collecting and analyzing the precipitated ondansetron powder. The flow rate of the solution, the temperature and the flow rate of the drying air, and other parameters are optimized so that the ondansetron precipitation is crystalline; and the particle size distribution is of about 0.5 to about 5 μm; and the mean volume diameter is of about 2-3 μm.

Alternatively, the powdered ondansetron of the aerosol and dry powder formulations may be prepared by dissolving the bulk ondansetron in supercritical fluid $CO_2$, to form a solution; depressuring the solution in a depressurization vessel; and collecting and analyzing the precipitated ondansetron powder. The temperature and the pressure of the SCF $CO_2$ (before the precipitation) and the depressurization vessel, and other parameters are optimized so that the ondansetron precipitation is crystalline; and the particle size distribution is of about 0.5 to about 5 μm; and the mean volume diameter is of about 2-3 μm.

For dry powder formulations, the powdered ondansetron may be mixed with one or more excipients, to form the dry powder formulation. The obtained dry powder formulation is then loaded into a dry powder inhaler. Alternatively, for pMDI formulations, the ondansetron may be mixed with a pressurized propellant or mixture of propellants, to form the pMDI formulation. The obtained pMDI formulation is then filled into canisters, which are installed into a metered-dose inhaler.

Thus, the present invention also provides pharmaceutical aerosol inhalation formulations or inhalable pharmaceutical aerosol formulations for pulmonary administration to a subject, wherein the formulation is a dry power formulation and comprises powdered ondansetron;
the powdered ondansetron is produced by a particle engineering process;
the MMAD of powdered ondansetron is between 1 and 3 microns;
the formulation may comprise excipient(s);
the formulation is administered into the pulmonary tract by inhalation; and
the subject is a cancer patient suffering from nausea that is related to chemotherapy, radiotherapy, or surgery;
or the formulation is a pMDI formulation comprises ondansetron;
the ondansetron may be powered ondansetron produced by a particle engineering process;

the MMAD of powdered ondansetron is between 1 and 3 microns;

the formulation may comprise excipient(s) and at least a hydrofluoroalkane;

the formulation is administered into the pulmonary tract by inhalation; and the subject is a cancer patient suffering from nausea that is related to chemotherapy, radiotherapy, or surgery.

The powdered ondansetron may be produced by a spray drying process that comprises:

i) dissolving the bulk ondansetron in distilled water, to form a solution;

ii) spray drying the solution in a spray dryer;

iii) separating and filtering the ondansetron particles according to their sizes with a cyclone; and iv) collecting and analyzing the precipitated ondansetron powder.

In another embodiment, the powdered ondansetron is produced by a supercritical fluid process that comprises:

i) dissolving the bulk ondansetron in supercritical fluid $CO_2$, to form a solution;

ii) depressuring the saturated solution in a depressurization vessel; and iii) collecting and analyzing the precipitated ondansetron powder.

In one embodiment, the formulation is a pharmaceutical dry powder inhalation formulation that contains lactose and/or glucose as an excipient, where the amount of ondansetron is about 0.05 to 100 wt %, about 1 to 50 wt %, about 2 to 20 wt %, or about 5 to 15 wt % of the excipient. In another embodiment, the formulation is a pharmaceutical pMDI inhalation formulation that contains P134a and/or P227 as propellants, where the amount of ondansetron is about 0.01 to 20 wt %, about 0.01 to 1 wt %, or about 0.01 to 0.5 wt % of the propellant.

Delivery of the pharmaceutical aerosol inhalation formulations into the pulmonary tract of a subject provides a Cmax of ondansetron in blood plasma that is about 20-80% of the Cmax achieved following intravenous bolus delivery of ondansetron. The Cmax from delivery into the pulmonary tract may be about the same as the Cmax achieved following oral delivery of ondansetron.

Delivery of the pharmaceutical aerosol inhalation formulations into the pulmonary tract of a subject provides Tmax of ondansetron in blood plasma that is less than the Tmax achieved following oral delivery of ondansetron.

Delivery of the pharmaceutical aerosol inhalation formulations into the pulmonary tract of a subject provides also provides an AUC of ondansetron in blood plasma that is about the same as the AUC achieved following intravenous bolus or oral delivery of ondansetron.

Additional embodiments within the scope provided herein are set forth in non-limiting fashion elsewhere herein and in the examples. It should be understood that these examples are for illustrative purposes only and are not to be construed as limiting in any manner.

Pulmonary Aerosol Formulations of the Present Invention

As described herein, the aerosol formulations of the present invention comprise ondansetron and the formulations are useful for pulmonary delivery via inhalation. The active drug ondansetron when administered by inhalation must penetrate deep into the lungs in order to show physiological action. In order to achieve this, the ondansetron inhaled should be in the powdered form. Preferably, the MMAD of ondansetron drug does not exceed about 5 µm.

Powdered Ondansetron

The powdered ondansetron can be prepared by processes of micronization, such as mechanical grinding, attrition by jet milling, solution precipitation, spray drying, lyophilization, and supercritical fluid processes.

Spray dying followed by a cyclone separation/filtering process may produce respirable particles rapidly and efficiently.

Direct controlled crystallization using an antisolvent precipitation technique may produce respirable particles with expected shapes. The particle size may be controlled by using one or more growth-retarding stabilizing additives.

Supercritical fluid processes may be used to produce respirable particles of the desired size. The supercritical processes may be used to prepare powdered ondansetron may include rapid expansion, solution enhanced diffusion, gas-anti solvent, supercritical antisolvent, precipitation from gas-saturated solution, precipitation with compressed antisolvent, aerosol solvent extraction system, or combinations of the foregoing. Particularly, the typical process can be rapid expansion of supercritical solution (RESS).

The powdered ondansetron prepared by the above processes may have an MMAD between 0.5 and 5 µm.

The amount of the powdered ondansetron in the formulation may be about 0.01% to about 100% of the total composition of formulation. Particularly, the amount of the powdered ondansetron may be 0.05% to about 20% of the total composition of formulation.

Dry Powder Formulations

Excipients

The aerosol formulations of the present invention may comprise pharmaceutically acceptable excipients. The typical excipients which may be used in the formulation include carbohydrates, amino acids, polypeptides, lipids, salts, polyalcohols, galactose, mannose, sorbose, lactose, glucose, trehalose, raffinose, maltodextrins, dextrans, mannitol, xylitol, alanine, glycine, tryptophan, tyrosine, leucine, phenylalanine, and mixtures or combinations thereof.

pMDI Formulations

Propellants

The pMDI formulations of the present invention may comprise pharmaceutically acceptable propellants. Typical propellants include hydrofluoroalkane (HFA) propellants. The hydrofluoroalkane propellants which may be used in the pMDI formulations include 1,1,1,2-tetrafluoroethane (P134a), 1,1,1,2,3,3,3-heptafluoro-n propane (P227), and mixtures of P134a and P227.

Surfactants

The pMDI formulations of the present invention may comprise pharmaceutically acceptable surfactants. Typical surfactants include alkylethers, alkyl arylethers, laurates, myristates, oleates, sorbates, stearates, propylene glycol, lipids, and combinations thereof.

Co-solvents

The pMDI formulations of the present invention may comprise pharmaceutically acceptable co-solvents. Typical co-solvents include $C_{2-6}$ alcohols, polyols, and combinations thereof. Particularly, the co-solvent may be ethanol.

EXEMPLARY FORMULATIONS OF THE INVENTION

The following examples illustrate certain embodiments of the disclosure and are not intended to be construed in a limiting manner.

Exemplary Formulations of the Invention

Formulation 1

| Ingredient | Amount |
| --- | --- |
| Ondansetron Fine Powder | 14 mg |

Formulation 2

| Ingredient | Amount |
| --- | --- |
| Ondansetron Fine Powder | 5 mg |
| Lactose Powder | 45 mg |

Formulation 3

| Ingredient | Amount |
| --- | --- |
| Ondansetron Fine Powder | 5 mg |
| Glucose Powder | 45 mg |

Formulation 4

| Ingredient | Amount |
| --- | --- |
| Ondansetron Fine Powder | 14 mg |
| Lactose Powder | 126 mg |

Formulation 5

| Ingredient | Amount |
| --- | --- |
| Ondansetron Fine Powder | 5 mg |
| Finer Lactose Powder | 4.5 mg |
| Coarser Lactose Powder | 40.5 mg |

Formulation 6

| Ingredient | Amount |
| --- | --- |
| Ondansetron Fine Powder | 14 mg |
| Glucose Powder | 126 mg |

Formulation 7

| Ingredient | Amount |
| --- | --- |
| Ondansetron Fine Powder | 5 mg |
| Finer Glucose Powder | 4.5 mg |
| Coarser Glucose Powder | 40.5 mg |

Formulation 8

| Ingredient | Amount |
| --- | --- |
| Ondansetron Fine Powder | 14 mg |
| Lactose Powder | 63 mg |
| Glucose Powder | 63 mg |

Formulation 9

| Ingredient | Amount |
| --- | --- |
| Ondansetron | 80 mg |
| HFA 134a Propellant | 10 g |

Formulation 10

| Ingredient | Amount |
| --- | --- |
| Ondansetron | 80 mg |
| HFA 134a Propellant | 10 g |
| Isopropyl Myristate | 0.1 g |

Formulation 11

| Ingredient | Amount |
| --- | --- |
| Ondansetron | 80 mg |
| HFA 227 Propellant | 10 g |

Formulation 12

| Ingredient | Amount |
| --- | --- |
| Ondansetron | 80 mg |
| HFA 227 Propellant | 10 g |
| Isopropyl Myristate | 0.1 g |

Formulation 13

| Ingredient | Amount |
| --- | --- |
| Ondansetron | 80 mg |
| HFA 134a Propellant | 20 g |

Formulation 14

| Ingredient | Amount |
| --- | --- |
| Ondansetron | 80 mg |
| HFA 227 Propellant | 20 g |

Formulation 15

| Ingredient | Amount |
| --- | --- |
| Ondansetron | 80 mg |
| HFA 134a Propellant | 10 g |
| HFA 227 Propellant | 10 g |

Formulation 16

| Ingredient | Amount |
| --- | --- |
| Ondansetron | 80 mg |
| HFA 134a Propellant | 10 g |

-continued

| Formulation 16 | |
|---|---|
| Ingredient | Amount |
| HFA 227 Propellant | 10 g |
| Isopropyl Laurate | 0.1 g |

| Formulation 17 | |
|---|---|
| Ingredient | Amount |
| Ondansetron | 8 mg |
| HFA 134a Propellant | 1 g |

| Formulation 18 | |
|---|---|
| Ingredient | Amount |
| Ondansetron | 8 mg |
| HFA 134a Propellant | 1 g |
| Isopropyl Myristate | 0.01 g |

| Formulation 19 | |
|---|---|
| Ingredient | Amount |
| Ondansetron | 8 mg |
| HFA 227 Propellant | 1 g |

| Formulation 20 | |
|---|---|
| Ingredient | Amount |
| Ondansetron | 8 mg |
| HFA 227 Propellant | 1 g |
| Isopropyl Myristate | 0.01 g |

| Formulation 21 | |
|---|---|
| Ingredient | Amount |
| Ondansetron | 8 mg |
| HFA 134a Propellant | 2 g |

| Formulation 22 | |
|---|---|
| Ingredient | Amount |
| Ondansetron | 8 mg |
| HFA 227 Propellant | 2 g |

| Formulation 23 | |
|---|---|
| Ingredient | Amount |
| Ondansetron | 8 mg |
| HFA 134a Propellant | 1 g |
| HFA 227 Propellant | 1 g |

| Formulation 24 | |
|---|---|
| Ingredient | Amount |
| Ondansetron | 8 mg |
| HFA 134a Propellant | 1 g |
| HFA 227 Propellant | 1 g |
| Isopropyl Laurate | 0.01 g |

Example 1

Preparation of Spray Dried Ondansetron Fine Powder

Powdered ondansetron was prepared by spray drying with SPRAY DRYER SD-MICRO™ (manufactured by GEA Process Engineering, Inc., Columbia, Md., USA). The experiments were done at GEA Process Engineering, Inc., Columbia, Md., USA.

TABLE 1

Parameters of Spray Drying to Prepare Ondansetron Fine Powder

| Run | Conc. (wt %) | $N_2$ (kg/hr) | Inlet Temp. (° C.) | Outlet Temp. (° C.) | Spray Rate (g/min) | Nozzle Diameter (mm) |
|---|---|---|---|---|---|---|
| 1 | 2.27 | 30 | 170 | 85 | 5.8 | 0.5 |
| 2 | 2.27 | 30 | 170 | 85 | 3.4 | 0.5 |
| 3 | 2.27 | 30 | 195 | 100 | 5.0 | 0.5 |

Example 2

Particle Size Distribution of Spray Dried Ondansetron Fine Powder

The Particle Size Distribution of the Ondansetron Fine Powder, prepared by Spray Drying using the above parameters was measured by Malvern Mastersizer (Malvern Instruments, UK) at GEA Process Engineering, Inc., Columbia, Md., USA.

Figure 2:
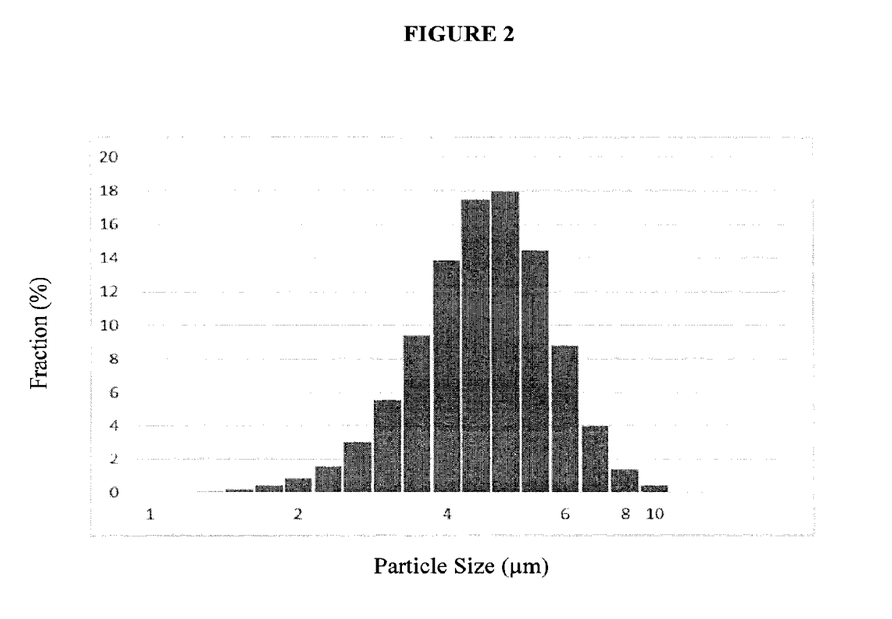
FIG. 2: A typical particle size distribution of spray dried ondansetron powder.

The typical Particle Size Distribution:
Mean Size: 4.80 μm
Std. Dev.: 1.59 μm
D10: 3.23 μm
D50: 5.01 μm
D90: 7.22 μm
Cumulative % on <10 μm: 99.5%

FIG. 2 shows the typical Particle Size Distribution of the Spray Dried Ondansetron.

Example 3

Fine Particle Fraction by Laser Diffraction

The Fine Particle Fraction (FPF) of the dry powder ondansetron aerosol formulations was measured by Laser Diffraction at Drug Dynamics Institute, College of Pharmacy, The University of Texas at Austin, Austin, Tex., USA.

The dry powder formulation measured by NGI included:
Spray Dried Ondansetron (SDO): 14 mg;
Excipient: None.

A Malvern Spraytec equipped with an inhalation cell and induction port was used for measuring the aerosol emitted from a HandiHaler® operated at 60 LPM. Neat SDO was filled into size 3 hypromellose capsules and inserted into the HandiHaler®. Measurements were carried out over a 4 second duration at 10 measurements/second. The Refractive Index used for SDO was 1.68 with an imaginary index of 0.01. Particles were assumed to be spherical.

The results showed that the FPF (defined as %<5.41 μm) of the dry powder ondansetron formulation was 15.6%.

Example 4

Fine Particle Fraction by Next Generation Impaction

The fine particle fraction (FPF) of the dry powder ondansetron aerosol formulations was measured by Next Generation Impaction (NGI) at Drug Dynamics Institute, College of Pharmacy, The University of Texas at Austin, Austin, Tex., USA.

The in vitro aerodynamic performance of the dry powder ondansetron aerosol formulations were tested by NGI. The results reflect the in vivo (pulmonary) aerodynamic performance of the following aerosol formulations. The Next Generation Impactor used in this embodiment was made by Copley Scientific, GB.

The Exemplary Formulation 1 (EF1) measured by NGI included:

Milled Ondansetron (MG): 14 mg;
Excipient: None The Exemplary Formulation 2 (EF2) that was measured by NGI was:
Milled Ondansetron (MG): 11.5 mg;
Coarse Lactose (LH201): 100 mg;
Fine Lactose: N/A.

The lactose in the EF2 was LACTOHALE® 201 (LH201; D10 was 3~6 μm, D50 was 2025 μm, D90 was 50~60 μm) made by DFE Pharma, Germany.

EF2 (SDO blended with Lactose) was prepared by a low shear mixing process, adapted for very low quantities of powder. SDO was incorporated into a LH201 by a three step dilution and spatchulation. The blend was then added to a scintillation vial and mixed by vortex mixing (1000 rpm, 15 sec, 5 cycles).

Handihaler® was used as the model Dry Powder Inhaler Device. The flow rate was 60 LPM (>4 kPa), the duration was 4 seconds, the total volume was 4 L. Testing was performed under ambient conditions. The ambient conditions were approximately 22° C. and 20% relative humidity (RH).

The number of NGI runs at ambient conditions were: EF1, n=5; EF2, n=4.

All NGI runs under ambient conditions exhibited a percent recovery greater than 90%. Aerosol particle size distribution (APSD) of individual NGI runs are given in FIGS. 3 and 4. Mean aerosol performance data are given in Table 2.

TABLE 2

The Mean APSD Parameters of EF1 and EF2 Measured by NGI at ~22° C. and 20% RH.

Figure 3:
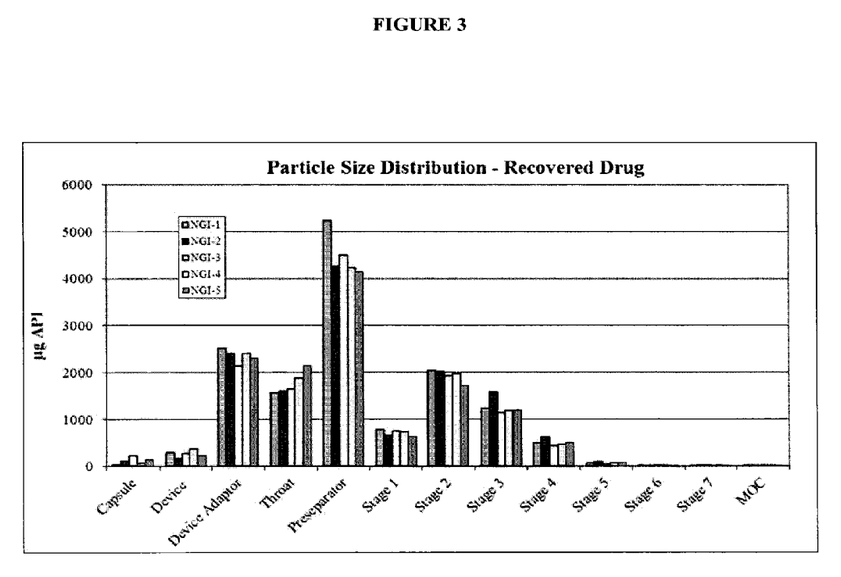
FIG. 3: The aerosol particle size distribution (ASPD) of 5 runs of the spray dried ondansetron under ambient temperature and humidity conditions of ~22° C. and 20% RH.
Figure 4:
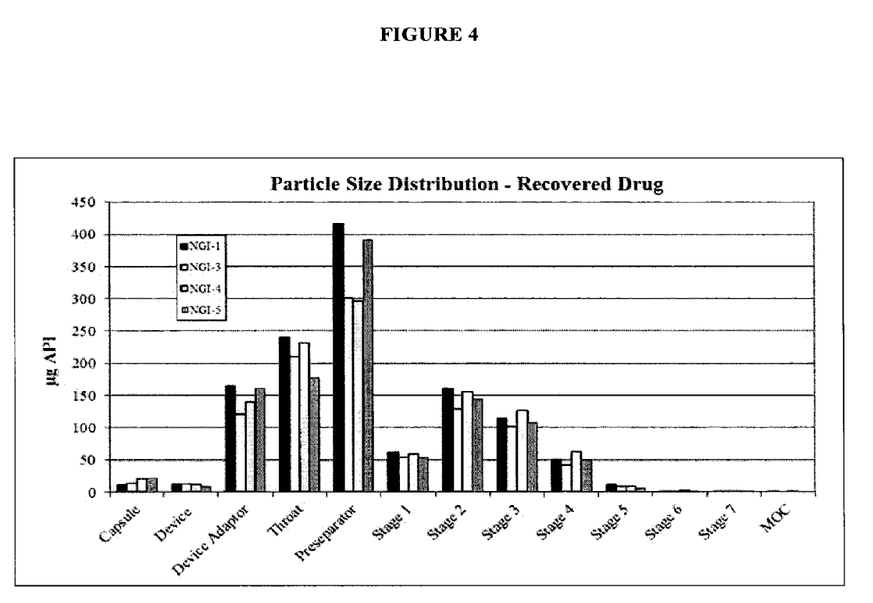
FIG. 4: The ASPD of 4 runs of the LH201 blend at 60 LPM and under ambient temperature and humidity conditions of ~22° C. and 20% RH.

| Parameter (Unit) | EF1 | RSD (%, EF1) | EF2 | RSD (%, EF2) |
|---|---|---|---|---|
| Amount of Drug Loaded (μg) | 14613.6 | 3.6 | 1114.7 | 7.3 |
| % Recovered | 92.3 | 3.2 | 100.4 | 5.2 |
| Preseparator, % of Loaded | 30.6 | 2.6 | 31.5 | 16.4 |
| Delivered Dose, % of Loaded | 89.7 | 3.9 | 97.8 | 5.3 |
| Fine Particle Fraction (≤5 μm), % of Delivered | 17.4 | 12.0 | 19.1 | 11.4 |
| Mass Median Aerodynamic Diameter(μm) | 4.97 | 4.3 | 4.69 | 2.1 |

The FPF of EF1 and EF2 under ambient conditions were 17.4 and 19.1%, respectively. FPF was defined as percent of particles less than 5 μm. The MMAD of EF1 and EF2-EF4 under ambient conditions was 4.97 μm, and 4.69 μm, respectively.

Example 5

Solubility of Ondansetron in pMDI Formulations

The solubility of ondansetron was measured in a pMDI medium of HFA 134 as well as a mixture of HFA 134 and ethanol.

The solubility results with HFA 134 alone were as follows:

| pMDI Medium | 8 days |
|---|---|
| HFA 134a (μg/mL) | 34.66 |
|  | 35.97 |
|  | 40.27 |
|  | 40.26 |
| Average (RSD) | 37.79 (0.077) |

As shown above, the solubility of ondansetron in a propellant alone, HFA 134a, was 37.79 μg/mL after 8 days. Since the gravity of the HFA 134a is 1.21 g/mL, the above results are equal to 0.00312% w/w.

The solubility of ondansetron in a mixture of HFA 134 and a cosolvent, ethanol, was also conducted. As shown in the following table, the solubility results were ondansetron 201.81 μg/mL after 8 days. The results are equal to 0.01668% w/w. ondansetron

| pMDI Medium | 8 days |
|---|---|
| HFA 134a with Ethanol (9:1) (μg/mL) | 199.48 |
|  | 196.85 |
|  | 215.75 |
|  | 195.17 |
| Average (RSD) | 201.81 (0.047) |

From the foregoing description, various modifications and changes in the compositions and methods provided herein will occur to those skilled in the art. All such modifications coming within the scope of the appended claims are intended to be included therein.

All publications, including but not limited to patents and patent applications, cited in this specification are herein incorporated by reference as if each individual publication were specifically and individually indicated to be incorporated by reference herein as though fully set forth.

REFERENCES

Hornby, P (2001). "Central neurocircuitry associated with emesis". The American Journal of Medicine 111 (8): 106S-112S. PMID 11749934

Cooke, C. E.; Mehra, I. V. (1994). "Oral ondansetron for preventing nausea and vomiting". American Journal of Hospital Pharmacy 51 (6): 762-771. PMID 8010314

Ye, J.-H.; Ponnudurai, R.; Schaefer, R. (2001). "Ondansetron: a selective 5-HT3 receptor antagonist and its applications in CNS-related disorders". CNS Drug Reviews 7 (2): 199-213. PMID 11474424

Chow, A. H.; Tong, H. H.; Chattopadhyay, P.; Shekunov, B. Y. (2007). "Particle engineering for pulmonary drug delivery". Pharmaceutical Research 24 (3): 411-437. PMID 17245651

The invention claimed is:

1. A dry powder aerosol formulation for use in a dry powder inhaler, comprising:
   ondansetron having a mean geometric diameter of 1-3 microns; and
   a pharmaceutically acceptable excipient,
   wherein the excipient is a mixture of coarse and fine particle lactose; and wherein the coares particle lactose has a D50 of about 55 μm or about 60 μm; and wherein the fine particle lactose has a D90 of equal to or less than 10 μm.

2. A method of treating nausea or vomiting, the method comprising: administering the formulation of claim 1 to a subject in need thereof, wherein the formulation is administered into the pulmonary tract of the subject by inhalation.

3. The formulation of claim 1, wherein the coarse lactose particle has a D10 of about 4 μm and D90 of about 170μm.

4. The formulation of claim 1, wherein ondansetron is about 30% of total composition of the formulation, or about 15% of the total composition of the formulation, or about 10% of the total composition of the formulation.

5. The formulation of claim 1 wherein the ratio of ondansetron to lactose is about 1:9.

6. The formulation of claim 1, wherein the ratio of coarse to fine lactose is about 9:1.

7. The formulation of claim 1, wherein ondansetron is more than about 1 mg and less than about 20 mg.

8. The formulation of claim 1, wherein ondansetron is more than about 2 mg and less than about 10 mg.

9. The formulation of claim 1, wherein the mass median aerodynamic diameter (MMAD) of ondansetron is between 0.5 and 5 microns.

10. The formulation of claim 1, wherein the mass median aerodynamic diameter (MMAD) of ondansetron is at least 2 microns; and at most 3.5 microns.

11. The formulation of claim 1, wherein the formulation has a fine particle fraction (FPF) of at least 55%, when tested using a Next Generation Impactor (NGI).

12. The formulation of claim 1, wherein the formulation has a respirable fraction (RPF) of 50% or more, when tested using a Next Generation Impactor (NGI).

13. The formulation of claim 1, wherein the formulation, when delivered through the pulmonary tract produces a mean area under curve (AUC) of ondansetron in blood plasma that is about 0.8 to 1.05 times of the mean AUC achieved following intravenous bolus delivery of ondansetron.

14. The formulation of claim 1, wherein the formulation, when delivered through the pulmonary tract produces a mean area under curve (AUC) of ondansetron in blood plasma that is about the same as the mean AUC achieved following intravenous bolus delivery of ondansetron.

15. The formulation of claim 1, wherein the formulation, when delivered through the pulmonary tract produces a maximal concentration (Cmax) of ondansetron in blood plasma that is about 0.2 to 0.6 times of the mean Cmax achieved following intravenous bolus delivery of ondansetron.

16. The formulation of claim 1, wherein the formulation, when delivered through the pulmonary tract produces a maximal concentration (Cmax) of ondansetron in blood plasma that is about 0.3 to 0.4 times of the mean Cmax achieved following intravenous bolus delivery of ondansetron.

17. The formulation of claim 1, wherein the formulation, when delivered through the pulmonary tract reaches maximum blood plasma concentration (Tmax) at about 5 min to about 30 min.

18. The formulation of claim 1, wherein the fine particle lactose has a D50 of less than 5 μm.

* * * * *